United States Patent [19]

Manjarrez

[11] Patent Number: 5,746,215
[45] Date of Patent: May 5, 1998

[54] IV INFUSION OR COLLECTION DEVICE WITH EXTENDABLE AND RETRACTABLE NEEDLE

[75] Inventor: Carlos H. Manjarrez, San Diego, Calif.

[73] Assignee: U.S. Medical Instruments, Inc., San Diego, Calif.

[21] Appl. No.: 742,040

[22] Filed: Nov. 1, 1996

[51] Int. Cl.$^6$ .................................. A61B 5/00
[52] U.S. Cl. ............. 128/763; 604/171; 604/197; 604/198
[58] Field of Search ............... 604/192, 193, 604/197, 198, 171; 128/760, 763

[56] References Cited

U.S. PATENT DOCUMENTS

| | | | |
|---|---|---|---|
| 3,890,971 | 6/1975 | Leeson et al. | 604/197 X |
| 4,542,749 | 9/1985 | Caselgrandi et al. | 128/763 X |
| 4,752,292 | 6/1988 | Lopez et al. | 604/244 |
| 4,767,413 | 8/1988 | Haber et al. | 604/198 |
| 4,782,841 | 11/1988 | Lopez | 128/164 |
| 4,813,426 | 3/1989 | Haber et al. | 128/763 |
| 4,846,805 | 7/1989 | Sitar | 604/165 |
| 4,915,702 | 4/1990 | Haber | 128/763 X |
| 4,950,250 | 8/1990 | Haber et al. | 604/192 |
| 4,957,490 | 9/1990 | Byrne et al. | 604/197 |
| 5,019,049 | 5/1991 | Haining | 604/198 X |
| 5,120,320 | 6/1992 | Fayngold | 604/177 |
| 5,192,275 | 3/1993 | Burns | 604/263 |
| 5,281,206 | 1/1994 | Lopez | 604/283 |
| 5,290,265 | 3/1994 | Davis et al. | 604/192 X |
| 5,304,144 | 4/1994 | Brimhall | 604/177 |
| 5,344,414 | 9/1994 | Lopez et al. | 604/283 |
| 5,423,758 | 6/1995 | Shaw | 128/763 X |
| 5,501,675 | 3/1996 | Erskine | 604/263 |
| 5,527,294 | 6/1996 | Weatherford et al. | 604/198 |

FOREIGN PATENT DOCUMENTS

WO 94/13337  6/1994  WIPO ................ 604/192

*Primary Examiner*—Sam Rivell
*Attorney, Agent, or Firm*—Brown, Martin, Haller & McClain

[57] ABSTRACT

An IV infusion or collection device with a needle being manually extended to a locked extendable position while extending a resilient member, and a lock-release mechanism for releasing the lock, whereby the resilient force retracts the needle into a shielding housing.

20 Claims, 7 Drawing Sheets

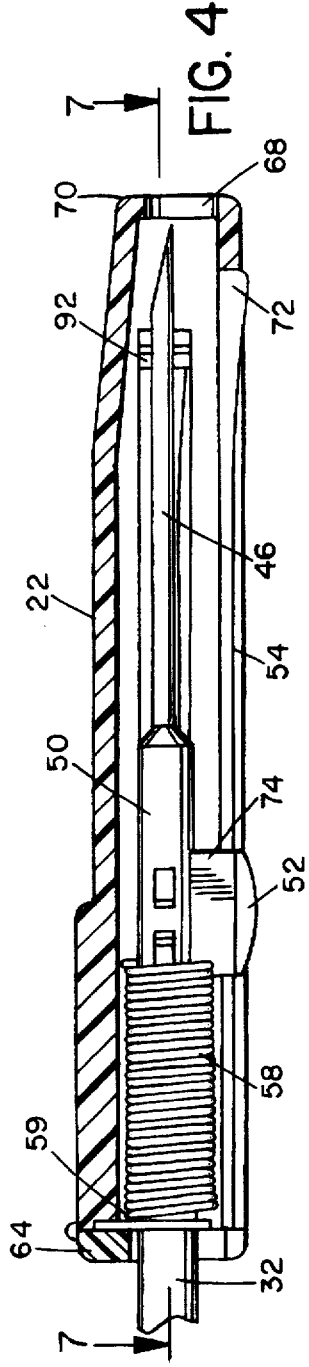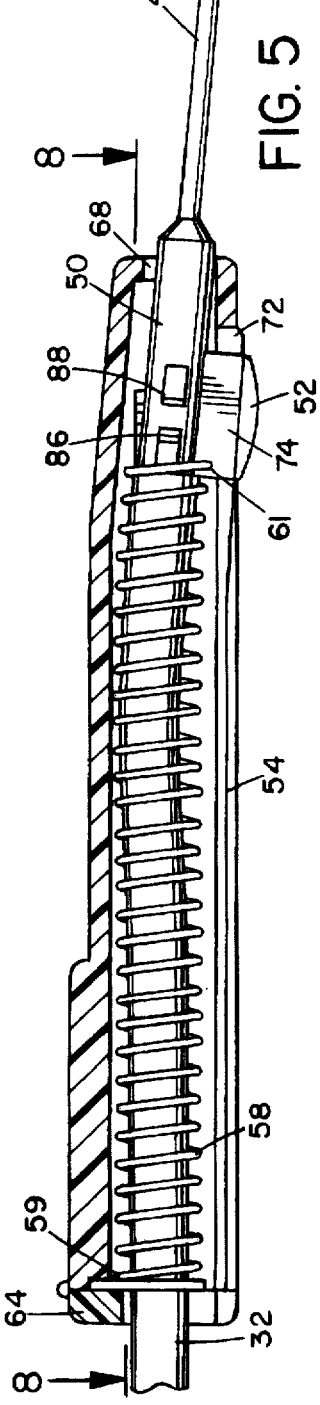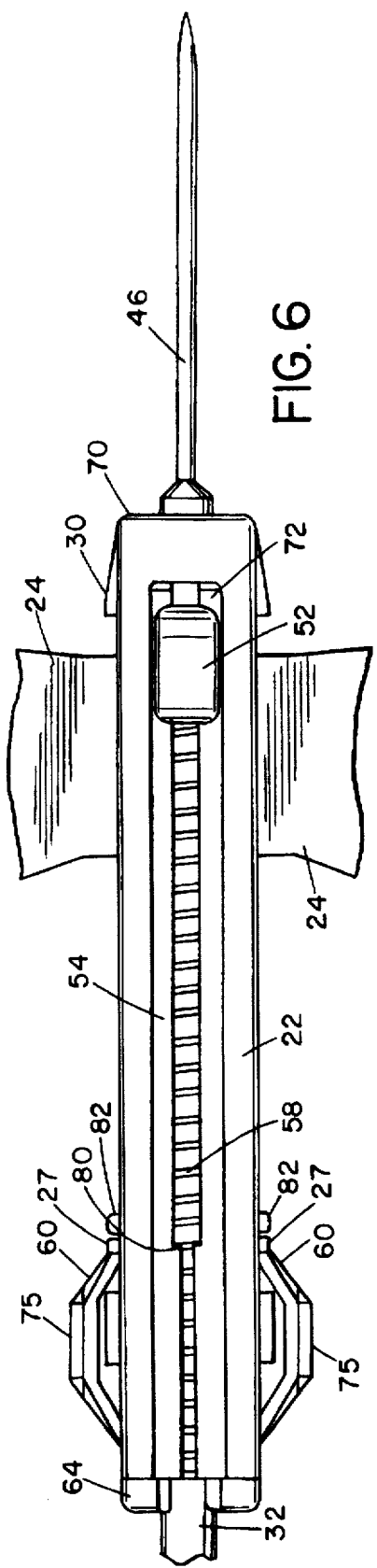

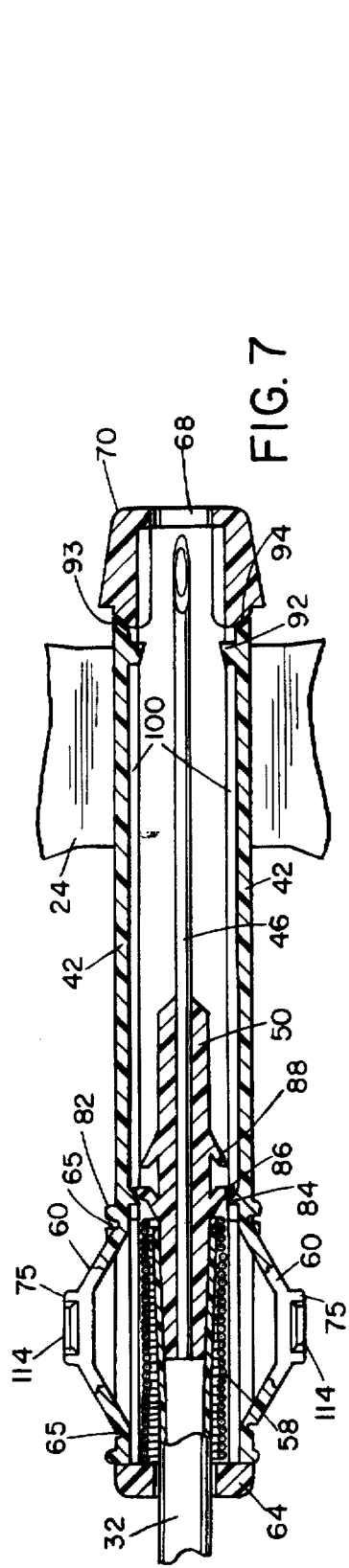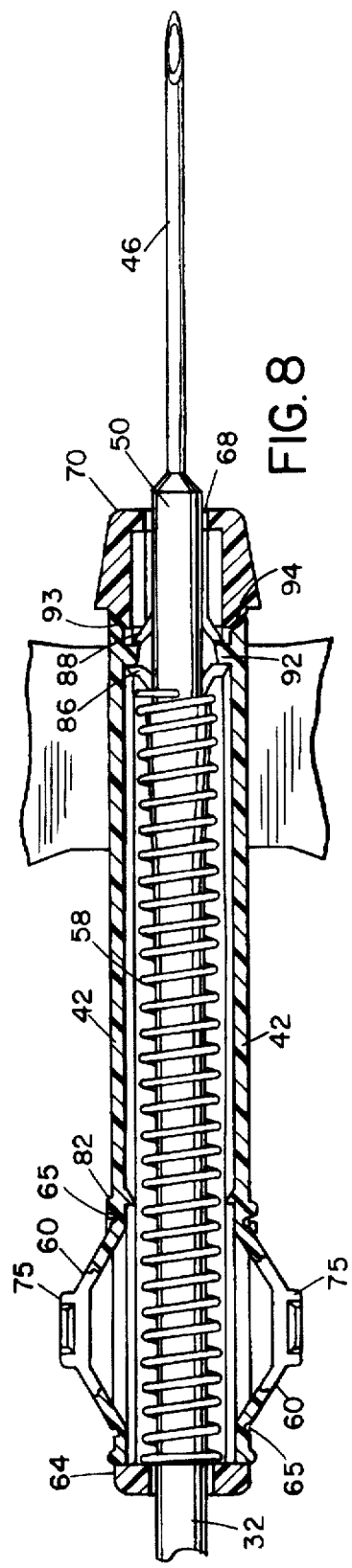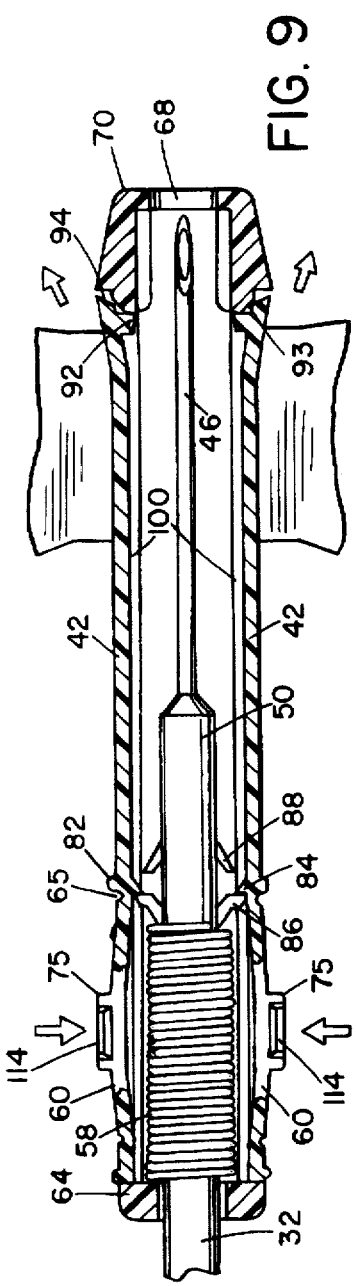

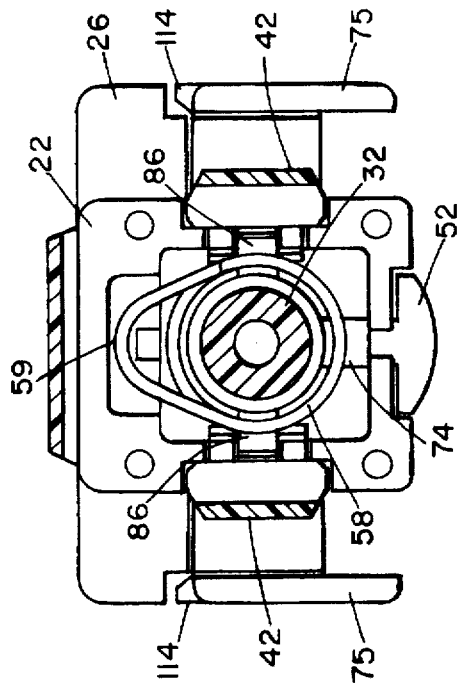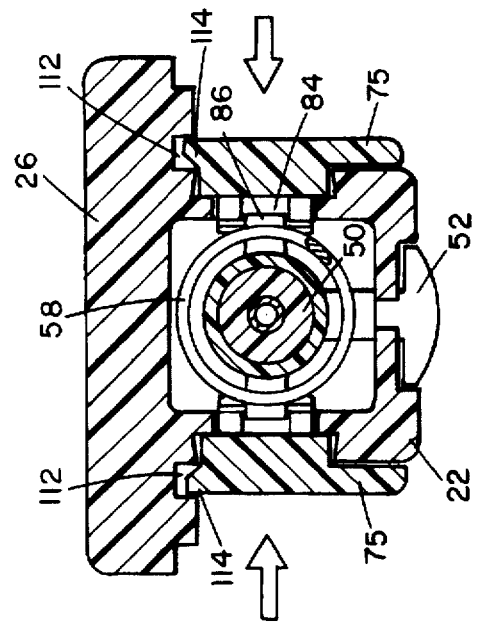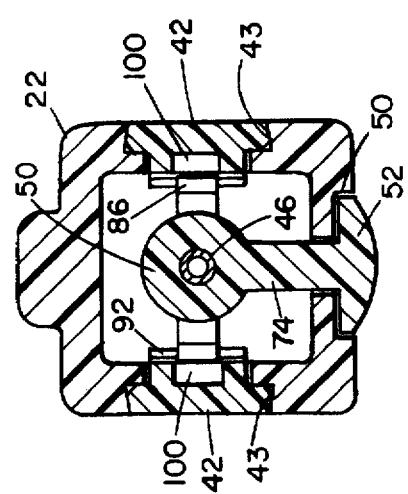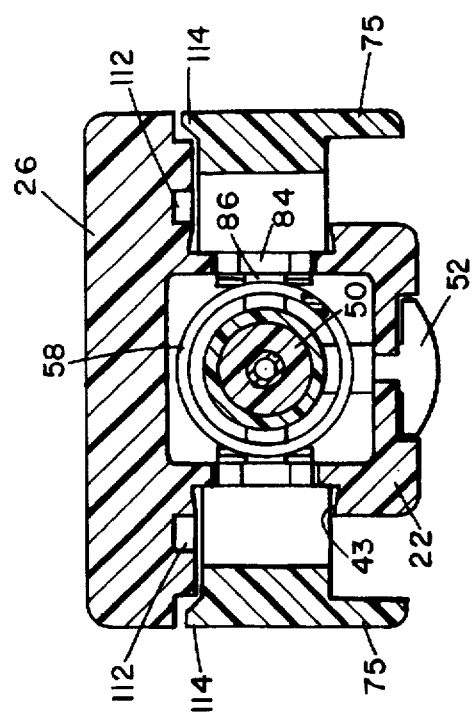

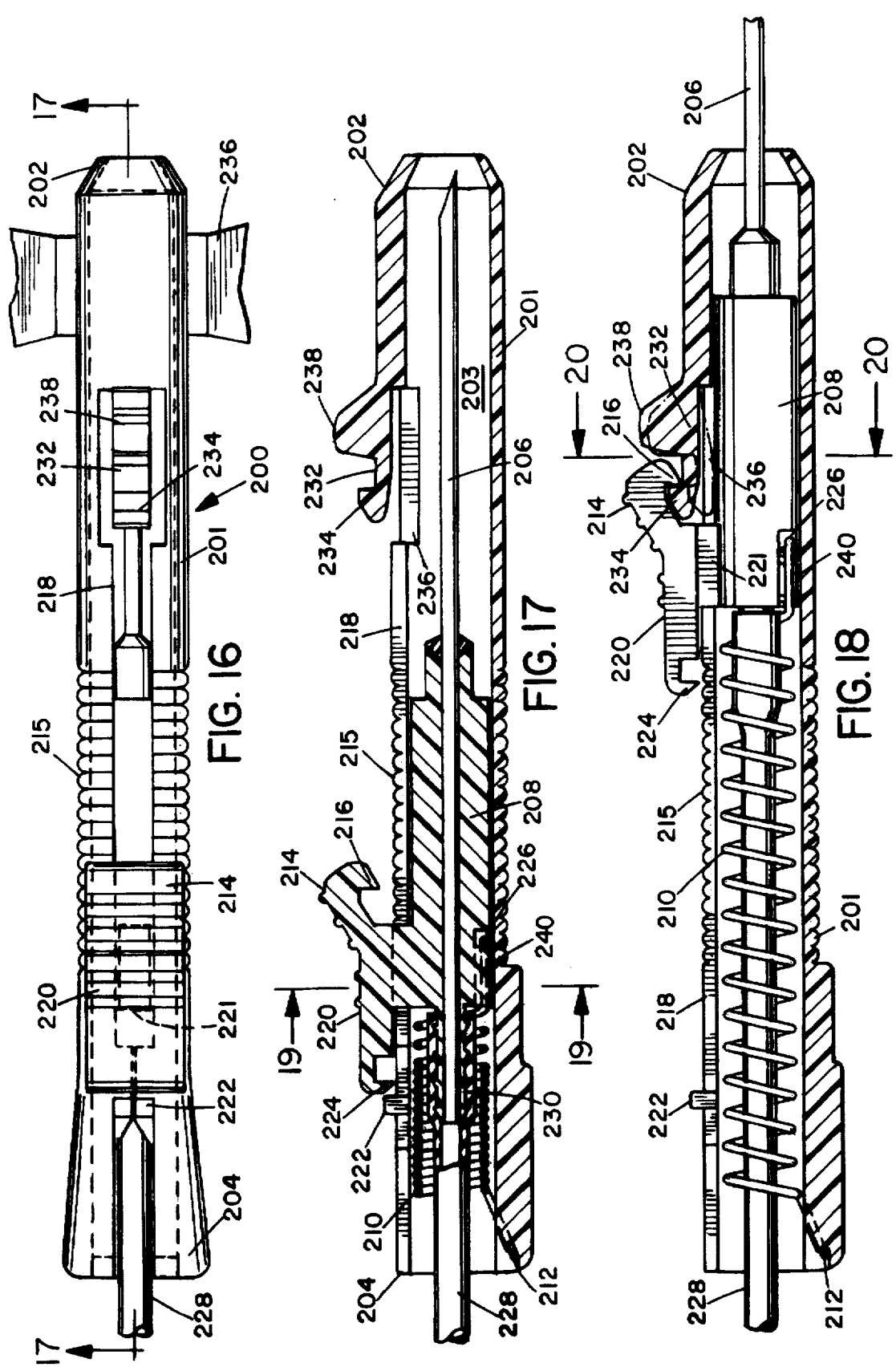

IV INFUSION OR COLLECTION DEVICE WITH EXTENDABLE AND RETRACTABLE NEEDLE

BACKGROUND OF THE INVENTION

The danger from needle sticks in the use of syringes, intravenous feeders, blood collection devices and the like is well known. There are several known devices that retract needle and needle holders into the barrels of syringes or provide a sliding outer cover over a needle projecting out at the end of a syringe to cover the needle after use. These retractable or covering devices are usually locked in position so it is difficult to re-use the syringe. After locking the needle in a covered condition, the unit with the needle can be placed in a sharp's container to be destroyed. This approach has not been applicable to intravenous feeders, blood collection devices or phlebotomy devices. Further, in almost all of the uses of needles to penetrate the human body, the devices are received with a needle projecting from the end thereof, or before the devices are used, a needle must be inserted into the syringe, IV infusion device or blood collecting device before it can be used. Not only does this require that a needle be separate from the device, but the needle has to be inserted at the time of use, or it must be shipped with the needle in place. The latter can have any of several disadvantages, some of which involve contamination of the needle, needle sticks from devices using needles where the user does not know whether the device or the needle in the device has been previously used, and just the general problems of shipping needles, IV intravenous feeder devices, or blood collecting devices with the needle sticking out. Although the needles can be sheathed, this is not always effective and the use of needle sheaths often lead to needle sticks. The re-mounting of needle sheaths on needles projecting from syringes and the like is exceedingly dangerous and can in itself lead to needle sticks.

Therefore it is an advantage to have an IV or blood collecting device in which the needle is in position in the housing and is projectable from the housing for use, is locked in the projected position and is then automatically retracted, after use, by merely releasing the locking mechanism.

SUMMARY OF THE INVENTION

This invention comprises an IV intravenous feeder or blood collecting device that uses a needle cannula and is particularly adaptable to a wing butterfly application. The device has a housing with a needle that is operatively connected, or can be operatively connected, to a flexible tubing or the like for intravenous feeding or blood collection. The needle is entirely shielded within the housing. A moving member is connected to the needle holder in the housing with an extension projecting outside the housing so that the moving member can be moved longitudinally in the housing, from outside, and thereby move the connected needle to a position where the needle projects out the end of the housing and is available for use and insertion into a user's vein. A resilient member, such as a tension spring in a relaxed condition, is connected between the movable member and the housing, and is extended resiliently, or stretched in movement of the needle to the extended position, where the needle and moving member are locked in position. The device is then used in the normal manner of a wing butterfly, by having the needle inserted into the vein and the butterfly being used to secure the position of the needle and the housing on the patient. After use, the housing and wing butterfly are released from the taped position in the normal manner, and the needle is withdrawn from the vein. A release mechanism is then actuated by a control outside of said housing that automatically unlocks or releases the needle and housing, allowing the resilient member to return to the tension state and also return the needle holder to the retracted position. The spring force automatically and immediately withdraws the needle to a position completely within the housing, thus providing protection against contact with the needle tip. The locking mechanism further locks the needle in this retracted position in a manner that makes it difficult to release the needle without deformation of the housing and the entire structure.

Accordingly, in this invention the needle is at all times contained within the housing, is only extended to a locked extended position for use, and after use, the lock mechanism is very easily released by operation of a finger-actuated lock release, wherein the needle is resiliently withdrawn into the housing, and locked in that position.

It is therefore an object of this invention to provide a new and improved device for retracting a needle into an enclosed housing after using the needle in an intravenous feeder, a blood collection device or in other similar devices.

It is a further object of this invention to provide a new and improved device for enclosing a needle in operable condition within a housing that is used for intravenous feeding or blood collection, which needle is unlocked from its retracted position, is extended to an extended position for use, is then locked in the extended position with the extending of the needle creating a resilient force, the resilient force is then released after use of the needle for immediate retraction within the housing where the needle is locked in position and cannot be removed.

Other objects and many intended advantages of this invention will become more apparent upon a reading of the following detailed description and an examination of the drawings in which the figures designate like parts throughout, and in which:

BRIEF DESCRIPTION OF THE DRAWINGS

FIG. 4 is a sectional view taken on line 4—4 of FIG. 1, with the needle retracted in ready-to-use position;

FIG. 5 is a similar sectional view with the needle extended;

FIG. 6 is a bottom plan view of the configuration shown in FIG. 5;

FIG. 7 is a sectional view taken on line 7—7 of FIG. 4;

FIG. 8 is a sectional view taken on line 8—8 of FIG. 5, showing the needle latched in the extended position;

FIG. 9 is a view similar to FIG. 8, but with the needle released and latched in the retracted position;

FIG. 12 is an enlarged sectional view taken on line 12—12 of FIG. 2;

FIG. 13 is an enlarged sectional view taken on line 13—13 of FIG. 2;

FIG. 14 is an enlarged sectional view taken on line 14—14 of FIG. 2;

FIG. 15 is a view similar to FIG. 14, with the buttons pressed inward to release the needle to the position shown in FIG. 9;

FIG. 16 is a top plan view of an alternative configuration of the IV set;

FIG. 17 is a sectional view taken on line 17—17 of FIG. 16;

FIG. 18 is a similar view with the needle extended;

DESCRIPTION OF THE PREFERRED EMBODIMENT

Figure 1:
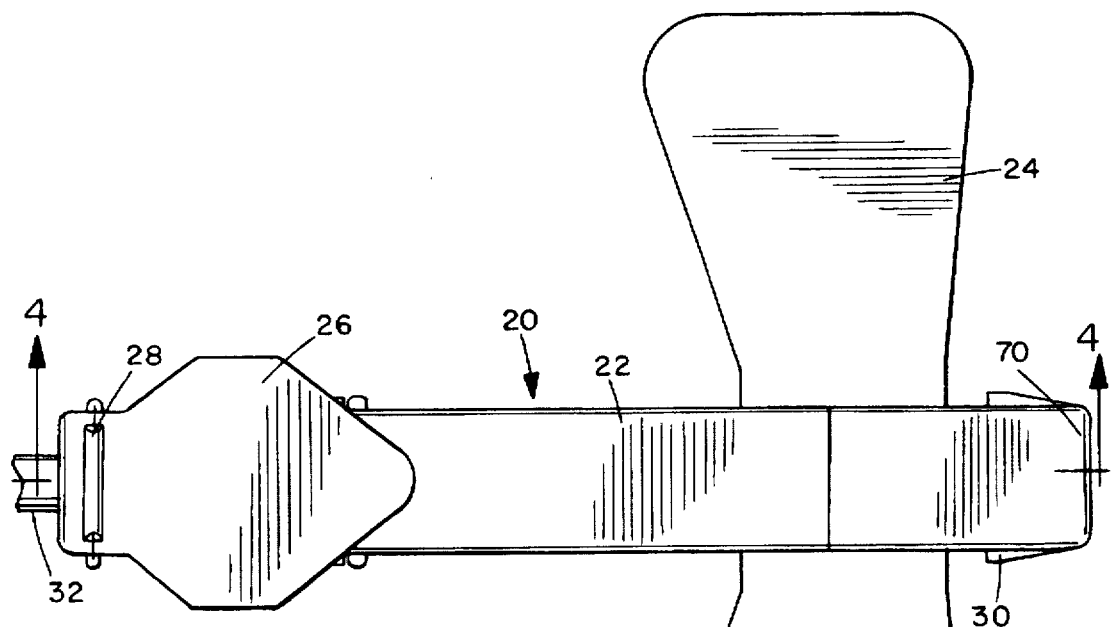
FIG. 1 is a top plan view of the IV set.
Figure 2:
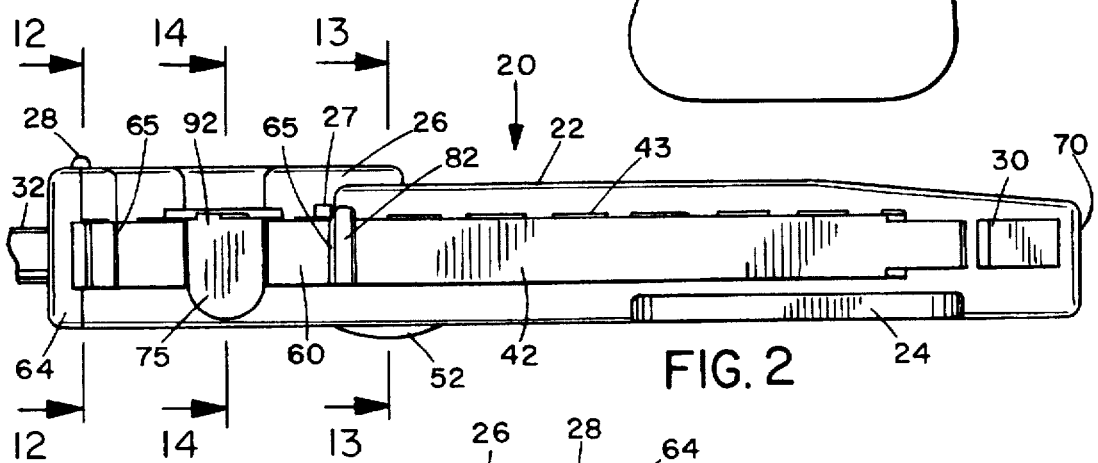
FIG. 2 is a side elevation view thereof.
Figure 11:
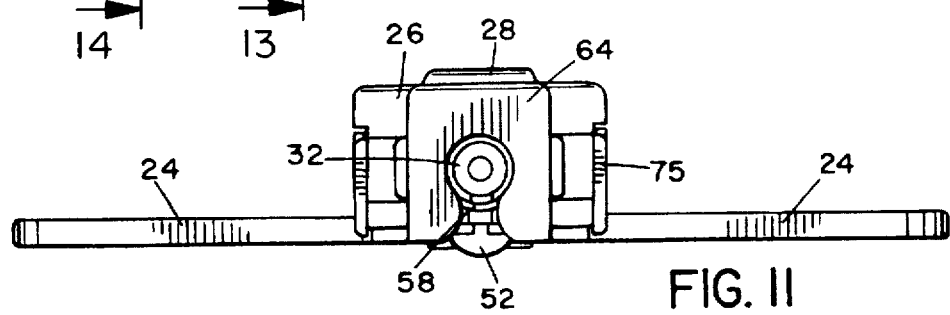
FIG. 11 is an end view as taken from the right hand end of FIG. 2.
Figure 3:
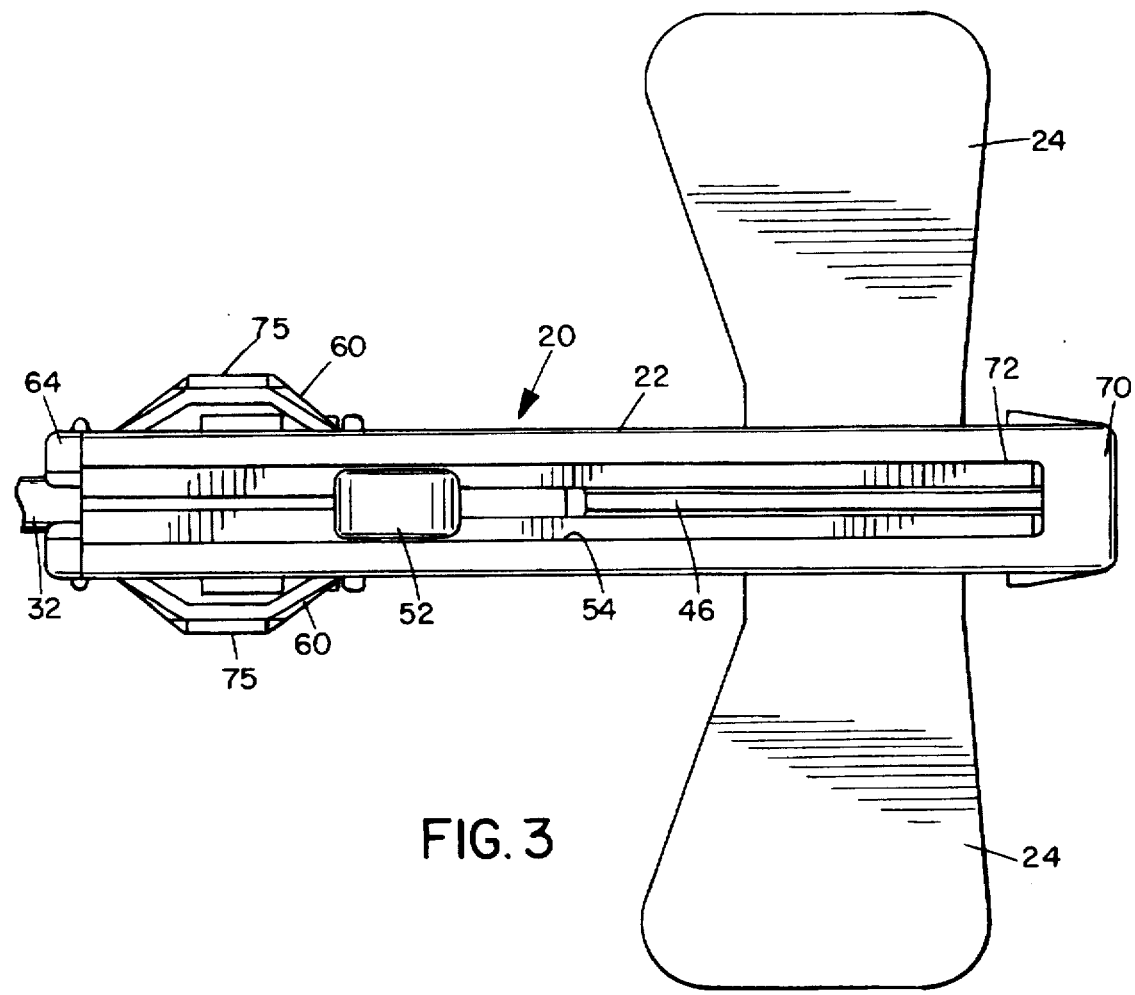
FIG. 3 is a bottom plan view thereof.
Figure 10:
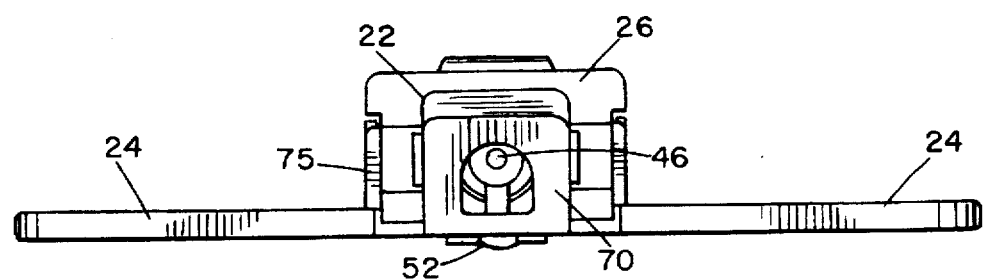
FIG. 10 is an end view as taken from the left hand end of FIG. 2.
Figure 20:
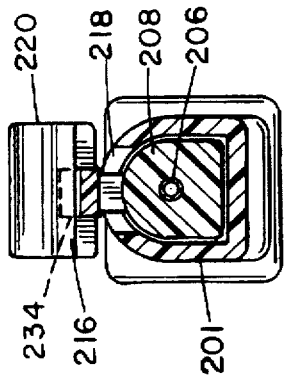
FIG. 20 is a sectional view taken on line 20—20 of FIG. 18.
Figure 19:
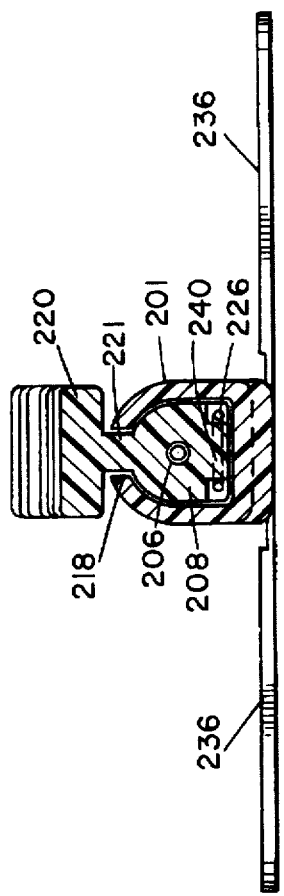
FIG. 19 is a sectional view taken on line 19—19 of FIG. 17.
Figure 21:
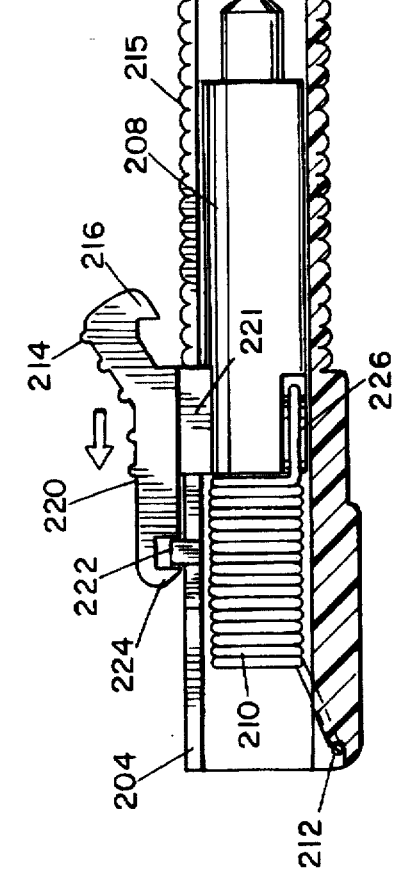
FIG. 21 is a view similar to FIG. 17, but with the needle carrier latched in retracted position.
Figure 22:
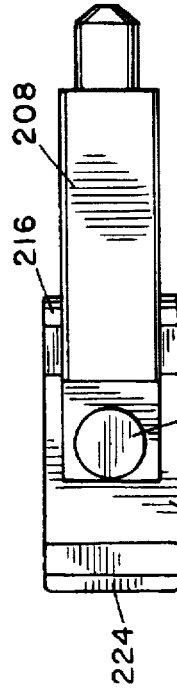
FIG. 22 is a bottom plan view of the needle carrier.

Referring now to FIG. 1, there is illustrated an IV infusion or blood collection device 20 with a body 22 and a butterfly wing 24 secured to body 22 in any known manner. In this top view, there is a handgrip cover 26 formed in the top side of the body that covers the mechanism for operating the slidable release arm, which cover is hinged into position by living hinge 28. A flexible tube 32 carries to or carries away fluids that will pass through this cannula needle that is positioned in housing 22.

Referring now to FIGS. 1, 2, 3 and 4, and specifically to FIG. 4, housing 22 has an upper top surface that is integral with handgrip 26, and a bottom surface with a distal end 70 having an opening for passing needle 46 therethrough and a flexible tube 32 for bringing fluid or taking fluid away from the needle. Tube 32 is secured in a fluid-tight connection with needle holder or carrier 50 through which cannula 46 projects. See FIG. 7. A button 52 is connected directly to needle holder 50 by shank 74. Tension spring 58 in housing 22 encircles needle holder 50. One end 59 of spring 58 is connected to housing 22, and the other end 61 of spring 58 is connected to needle holder 50. Coil spring 58 is a tension spring that is in its rest position in FIG. 4. Shank 74 and button 52 move through a channel 54 along the length of the tubular volume of housing 22.

The device is in position for use as illustrated in FIG. 4. It is contemplated that the invented device would be shipped in this condition either connected or not connected to flexible tube 32, with the needle cannula in the retracted, housed condition. When the device is to be used, then the device is readied by moving button 52 forward to the other end of channel 54 to a position just adjacent end ramp section 72 of channel 54, see FIGS. 5 and 6. This moves the innerly connected needle housing 50 and cannula 46 to the forward position with needle 46 extending out end 68 of distal end 70 of housing 22. The housing is curved or inclined downward to provide a better trajectory for needle 46 being inserted into a patient's vein. In this position, needle carrier or holder 50 is locked in the needle extended position with spring 58 tensioned and poised for retracting needle holder 50 and cannula needle 46 back into housing 22 in a manner that will be described.

Referring to FIGS. 7, 8 and 9, needle carrier 50 has a rear permanent lock tab 86 that is cantilevered to project outwardly into a side channel 100 that extends the length of housing 22. A forward semi-lock tab 88 is also cantilevered from the side of needle housing 50. Similar lock tabs, semi-lock tabs and side channels 100 are on each side of needle carrier 50 and housing 50, as illustrated in FIG. 7. Each channel 100 has a semi-lock rib 92 that coacts with tabs 86 and 88 to lock and release needle carrier 50 in the forward and extended position. In the relaxed or non-extended position of FIG. 7, rear permanent lock tab 86 rests against a permanent lock rib 84. Needle carrier 50 in this relaxed condition is available for forward movement. As previously described, to make the device in a condition for use, actuating button 52 is pushed forward in longitudinal slot 54 until tab 88 contacts forward lock rib 92 at which time tab 88 is cammed downwardly and passes over rib 92, and then flexes back to the locked position as illustrated in FIG. 8. Further forward movement of the button and needle carrier 50 is restricted by tab 86 contacting the rear side of rib 92. In this position, the needle holder is locked against the either forward or rearward movement. Accordingly, the device can thus be used in the normal manner by inserting the distal end of needle cannula 46 into a patient's vein.

Housing 22 has longitudinal, inwardly beveled slots 43 in each of the opposite sides of the housing. See FIG. 13. Longitudinal members 42, which are slidable release arms, fit into slots 43 in a dove tail, slidable connection. The outer longitudinal edges of slidable release arm 42 snap into the dove tail connection along the entire length of arm 42. In the rest position, see FIG. 7, release arm 42 has an angled-forward edge 94 that abuts against an angled surface at the end of slot 43 at end 72. The other end of each of release arms 42 abuts against end cap 64, with slidable release arm actuating means 60 that comprises outwardly flexed bridge 60.

Flexed out bridge 60 comprises three sections that are bent at their intersections, which sections are also undercut at 65 to facilitate the flexing action of the bridge support. Center bridge section 75 forms the inward push member for collapsing the bridge and forcing section 41 to slide in the dove tail connection toward distal end 72 of housing 22. Permanent lock rib 82 prevents outwardly flexing of arm 42 forward of rib 82, so that the flexing in and out of bridge 60 is limited to that between end 65 and rib member 82 of arm 42.

Extended bridge 60 comprises a finger-operated release mechanism which can be compressed from the position illustrated in FIG. 14 to the collapsed condition in FIG. 15. This pressure is exerted by the user's fingers which contact the respective surfaces 75 and squeeze the two extended bridges 60 together. Slidable release arm 42 movement toward distal end 70 causes beveled end 94 to slide forward and outward on lead out ramp 93, which moves and in turn lifts semi-lock rib 92 outward and out of contact with rear permanent lock tab 86 and forward semi-lock tab 88. This releases needle holder 50 from the locked condition, and allows tension spring 58 to contract. The force of the spring 58 pulls needle holder 50 and needle cannula 46 to the retracted position of FIG. 9, where both are fully retracted into housing 22. Rear permanent lock tab 86 is depressed by permanent lock rib 84, which tab 86 flexes back to normal, and abuts rib 84, locking needle holder 50 in the retracted position. The forward edge of semi-lock rib 92 in turn abuts against the lower side of ramp 94, restricting and preventing further movement of the slidable release arm in the forward direction. In collapsing bridge 60 by the squeezing force applied in the direction of the arrows in FIG. 9, the three sections 60 are flattened. This continued force causes the upper angled ridge edges 114 to be cammed downward along the ramp edge and the ridge then slides into slots 112.

This secures section 60 from outward movement. See FIG. 15. Spring 58 has fully retracted with the needle housing and cannula needle 46 fully enclosed in a locked condition within housing 22. Needle 46 cannot be further used, is not subject to inadvertent needle sticks, and device 20 and its tubing can be suitably disposed of.

In another embodiment, see FIGS. 16 through 22, a wing butterfly device 200 comprises a housing 201 with a normal wing 236 attached. Housing 201 has a hollow tubular channel therethrough with a proximal end 204 and a distal end 202. Housing 201 has a longitudinal slot 218 through the upper wall of housing 201. Positioned in the housing is a needle holder 208 that may be cylindrical and fits the tubular configuration of volume 203 in housing 201. An outward projecting operational finger actuated member 220 has a relatively wide upper surface that is connected to a narrow rib 221 that in turn is connected to the side of a needle carrier 208. When positioned in the housing, with actuating member 220 projecting above slot 218, forward and reverse movement of member 220 moves needle holder 208 in a corresponding forward and reverse direction in volume 203. Forward movement of needle carrier 208 projects needle cannula 206 out distal end 202 for use in intravenous feeding or blood collection functions. Connected to the rear end of needle holder 208 is a barbed tube end that receives and holds flexible connecting tube 228 for fluid passage. Mounted around tube 230 is a coiled tension or extension spring that is connected at its rear end to housing 201 in slot 212, and is connected at its front end by coiled end 226 of the spring around post 240.

As illustrated in FIG. 17, in the rest position, the two locking, hook ends 216 and 224 of finger-actuating member 220 are unconnected and unlocked. On the forward end of housing 220 is a cantilevered locking member 232, having a hooked or barbed end 234. Hook end 234 is shaped to coact with hook end 216 on finger-actuating member 220.

IN OPERATION

In operation, in the ready condition for use, device 200 is in a rest condition with spring 210 unextended and needle 206 retained in and sheathed by housing 201. To ready the device for use, the user pushes forward finger-actuating member 220 which slides in slot 218 to the position illustrated in FIG. 18. This movement stretches spring 210 and also projects needle 206 through distal end 202. Needle carrier's finger-actuated hook 214 is moved forward until hook end 216 contacts forward hook end 234. Forward hook end 234 comprises a cantilevered member 232 that flexes or bends at 242 into recess 236. So when end 216 contacts hook end 234, hook end 234 flexes downward allowing hook end 216 to engage hook end 234, locking needle carrier 208 in the extended position. In this position, needle cannula 206 is capable of being inserted into the vein of a user with fluid passing to and from the vein through the needle cannula to flexible tubing 228. The resilience of spring 210 in exerting a retracting force, holds needle carrier 208 in the locked position.

After use, needle 206 is removed from the patient's vein and the user's finger is pressed against surface 238 of cantilevered lock member 232. This flexes hook 234 into recess 236, unlocking and freeing needle holder 208 to be quickly withdrawn by the spring that retracted to its original position of FIG. 17. The movement of the spring is such that it forces rear hook 224 to move a sufficient rearward distance so that hook 234 cams over lock rib 222. This locks the needle carrier and needle 206 to an enclosed position within housing 221. In this position, the needle is thus sealed within the housing and is not available for contact.

Figure 23:
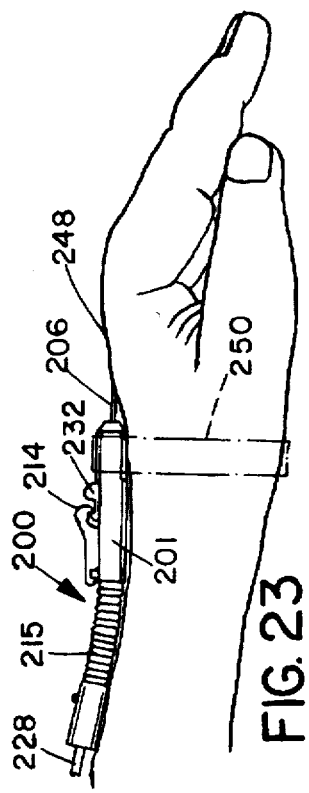
FIG. 23 is a side view of the use of the IV set in use, using the housing bending capability.

The housing and all the parts in each embodiment, except the spring and needle, may be made of any suitable plastic. The housing has a coil type surface 215 for grasping when using the device. Also, as illustrated in FIG. 23, said plastic section 215 is capable of flex, bending to fit the configuration of the patient in various actual uses of the device.

Although some preferred embodiments of the present invention have been described above by way of example only, it may be understood by those skilled in the field that modifications may be made to the disclosed embodiments without departing from the scope of the invention which is defined by the appending claims.

I claim:

1. An IV or blood collection device comprising:
    a housing having a proximal end and a distal end with a movable needle carrier operatively positioned for movement in said housing from a retracted position at said proximal end of said housing to an extended position at said distal end of said housing, and then to a shielded, said retracted position;
    a stretchable resilient member connected between said needle carrier and said housing;
    an actuating member that moves said needle carrier from said retracted position to said extended position while stretching said resilient member;
    a releasable locking device that locks said needle in said extended position;
    a lock-releasing device that releases said releasable locking device, whereby said resilient member retracts said needle carrier to said retracted position within said housing; and
    a lock device that locks said needle carrier in said retracted position within said housing.

2. An IV or blood collection device as claimed in claim 1 wherein,
    said actuating member is positioned outside said housing and coacts with said needle carrier in moving said needle carrier in said housing.

3. An IV or blood collection device as claimed in claim 2 wherein,
    said housing having a wall with a slot through said wall;
    said actuating member having an extension member that connects to said needle carrier through said slot; and
    said extension member being movable in said slot in response to moving said actuating member from outside said housing in moving said needle carrier.

4. An IV or blood collection device as claimed in claim 1 wherein,
    said releasable locking device comprising a first lock element connected to said needle carrier and a second lock element connected to said housing; and
    said first lock element being moved with said needle carrier to engage said second lock element, locking said needle carrier in said extended position.

5. An IV or blood collection device as claimed in claim 4 wherein,
    said releasable locking device including said first lock element and said second lock element being positioned outside said housing.

6. An IV or blood collection device as claimed in claim 5 wherein,
    said lock device has a third lock element connected to said needle carrier and a fourth lock element connected to said housing at said proximal end; and said third lock element contacts said fourth lock element in locking said needle carrier in said retracted position.

7. An IV or blood collection device as claimed in claim 6 wherein, said releasable locking device and said lock device and said lock releasing device are located outside of said housing.

8. An IV or blood collection device as claimed in claim 6 wherein, said releasable locking device and said lock device are positioned within said housing and said lock releasing device is positioned both inside and outside said housing.

9. An IV or blood collection device as claimed in claim 6 wherein, said housing having a wall with a slot through said wall;

said actuating member having an extension member connected to said needle carrier and projecting through said slot, and having an outer member for manual movement.

10. An IV or blood collection device as claimed in claim 9 wherein, said outer member of said extension member has a first hook end;

a second hook end connected to the outer surface of said housing at said distal end; and said first hook end is engageable with said second hook end to lock said needle carrier in said extended position.

11. An IV or blood collection device as claimed in claim 10 wherein, said extension member having a rearwardly directed hook end;

a rib having a projected shoulder secured to said housing adjacent the proximal end of said housing; and said rear hook end engaging said rib upon movement of said needle carrier, locking said needle carrier in said retracted position.

12. An IV or blood collection device as claimed in claim 11 wherein, said second hook end on said housing comprising a cantilevered flexible member that projects over a slot in the adjacent side of said housing, whereby said cantilevered flexible extension is flexed towards said slot, disengaging said second hook end from connection with said first hook end, releasing said releasable lock device;

whereby said resilient member retracts said needle carrier to said retracted position.

13. An IV or blood collection device as claimed in claim 1 wherein:

said stretchable resilient member comprises a coil spring coiled around one end of said needle carrier adjacent said proximal end of said housing.

14. An IV or blood collection device as claimed in claim 6 wherein, said releasable locking device comprising a first tab extending outward from said needle carrier in said housing;

a longitudinal slidable panel in the side of said housing with a tab on the inside of the panel projecting into said housing; and said needle carrier tab coacting and abutting against said panel tab when said needle carrier is moved by said actuating member to said extended position.

15. An IV or blood collection device as claimed in claim 14 wherein, said panel having a finger-collapsing bridge that moves said panel in a forward direction toward the distal end of said housing; and said forward end of said panel contacting the distal end of said housing, causing said forward end of said panel to move outwardly moving said panel tab outwardly from contact with said first tab on said needle carrier, unlocking said needle carrier for retraction by said resilient member to said retracted position.

16. An IV or blood collection device as claimed in claim 15 wherein, said needle carrier having a second outwardly projecting tab and said panel having a second inwardly projecting tab; and said first needle carrier tab abutting said rear side of said second panel tab, in rearward movement of said needle carrier by said resilient member, locking said needle carrier in said retracted position.

17. An IV or blood collection device as claimed in claim 16 wherein, said first tab abuts the forward side of said second tab on said panel when said needle carrier is in said retracted position, locking said needle carrier from further rearward movement housing in said retracted position.

18. An IV or blood collection device as claimed in claim 17 wherein, said panel having a flexible outward extended integral bridge section adjacent the proximal end of said housing; and said flexible bridge section subject to inward compression force by the fingers of a user to compress said flexible bridge member forcing said panel in said forward movement to lock said releasable locking device.

19. An IV or blood collection device as claimed in claim 18 wherein, said housing having a side panel slot on each side in which said panels are inserted;

adjacent edges of said panel and the inner side edges of said panel slot, engaging in a dove tail connection allowing sliding movement of said panel in said panel slot.

20. An IV or blood collection device as claimed in claim 19 wherein, said panel slot having an end wall edge in said distal end of said housing, which has a beveled surface; and the adjacent edge of the end of said panel having a beveled surface that coacts with said end wall beveled surface, which beveled surfaces provide a ramp surface on which the forward end of said panel is cammed outwardly in forward movement of said panel to move said first lock tab outward from said housing, releasing said releasable lock device.

* * * * *